US012327354B2

(12) United States Patent
Krafft et al.

(10) Patent No.: US 12,327,354 B2
(45) Date of Patent: Jun. 10, 2025

(54) APPARATUS, SYSTEM AND METHOD FOR SUPPORTING A PROCEDURE OF AN IMAGING EXAMINATION

(71) Applicant: Siemens Healthineers AG, Forchheim (DE)

(72) Inventors: Axel Joachim Krafft, Hemhofen (DE); Florian Maier, Buckenhof (DE); Manuel Schneider, Unterföhring (DE); Dirk Franger, Erlangen (DE); Ralf Vogel, Fürth (DE)

(73) Assignee: Siemens Healthineers AG, Forchheim (DE)

( * ) Notice: Subject to any disclaimer, the term of this patent is extended or adjusted under 35 U.S.C. 154(b) by 323 days.

(21) Appl. No.: 17/851,301

(22) Filed: Jun. 28, 2022

(65) Prior Publication Data

US 2022/0414877 A1    Dec. 29, 2022

(30) Foreign Application Priority Data

Jun. 29, 2021 (DE) .......................... 102021206761.1

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0013* (2013.01); *A61B 5/055* (2013.01);
(Continued)

(58) Field of Classification Search
CPC ................. G06T 7/0012; G06T 19/006; G06T 2207/30004; G06T 2207/30204;
(Continued)

(56) References Cited

U.S. PATENT DOCUMENTS 7,376,903 B2 * 5/2008 Morita ..................... G06F 3/011
715/701
10,462,451 B1 * 10/2019 Trail ................... G01B 11/2513
(Continued)

FOREIGN PATENT DOCUMENTS

DE     102015216917 A1    3/2017
DE     102015226669 A1    6/2017

OTHER PUBLICATIONS

Augmented Reality for Interventional MRI Procedures; published Jun. 16, 2021.

*Primary Examiner* — Santiago Garcia
(74) *Attorney, Agent, or Firm* — Banner & Witcoff Ltd.

(57) ABSTRACT

The disclosure relates to an extended-reality device having an interface, a computing unit, and a user interface. The extended-reality device may be configured to capture, using the interface, a procedure of an imaging examination using an imaging apparatus. The computing unit may be configured to determine information concerning the procedure of the imaging examination and to provide said information to a user of the extended-reality device using the user interface. The disclosure further relates to a system including an imaging apparatus with an extended-reality device, and to a method for providing information concerning a procedure of an imaging examination using the system.

15 Claims, 5 Drawing Sheets

(51) Int. Cl.
*A61B 5/055* (2006.01)
*G06F 3/01* (2006.01)
*G06F 3/03* (2006.01)
*G06T 19/00* (2011.01)

(52) U.S. Cl.
CPC ............ *A61B 5/7425* (2013.01); *G06F 3/012* (2013.01); *G06F 3/013* (2013.01); *G06F 3/0304* (2013.01); *G06T 19/006* (2013.01); *G06T 2207/30004* (2013.01); *G06T 2207/30204* (2013.01); *G06T 2210/41* (2013.01)

(58) Field of Classification Search
CPC ... G06T 2210/41; A61B 5/0013; A61B 5/055; A61B 5/7425; A61B 5/1127; A61B 5/704; A61B 5/706; A61B 5/0077; G06F 3/012; G06F 3/013; G06F 3/0304; G06F 3/011
See application file for complete search history.

(56) References Cited

U.S. PATENT DOCUMENTS

| | | | | |
|---|---|---|---|---|
| 10,959,791 | B2* | 3/2021 | Bonutti | A61B 17/8802 |
| 11,861,898 | B2* | 1/2024 | Prevrhal | G06F 30/10 |
| 2012/0226141 | A1* | 9/2012 | Shinoda | G01R 33/543 |
| | | | | 600/419 |
| 2017/0069120 | A1* | 3/2017 | Benner | G06F 3/013 |
| 2017/0186157 | A1* | 6/2017 | Boettger | A61B 5/0013 |
| 2017/0236275 | A1* | 8/2017 | Jung | A61B 8/5223 |
| | | | | 382/131 |
| 2018/0357825 | A1* | 12/2018 | Hofmann | A61B 34/20 |
| 2020/0170534 | A1* | 6/2020 | Flaeschner | A61B 5/742 |
| 2020/0342228 | A1* | 10/2020 | Prevrhal | G06V 20/20 |
| 2022/0172351 | A1* | 6/2022 | Lee | G16H 30/40 |
| 2022/0239869 | A1* | 7/2022 | Soluch | G01R 33/283 |
| 2023/0410301 | A1* | 12/2023 | Rajagopal | G06T 7/12 |
| 2024/0004470 | A1* | 1/2024 | Van Dooren | G16H 20/70 |

* cited by examiner

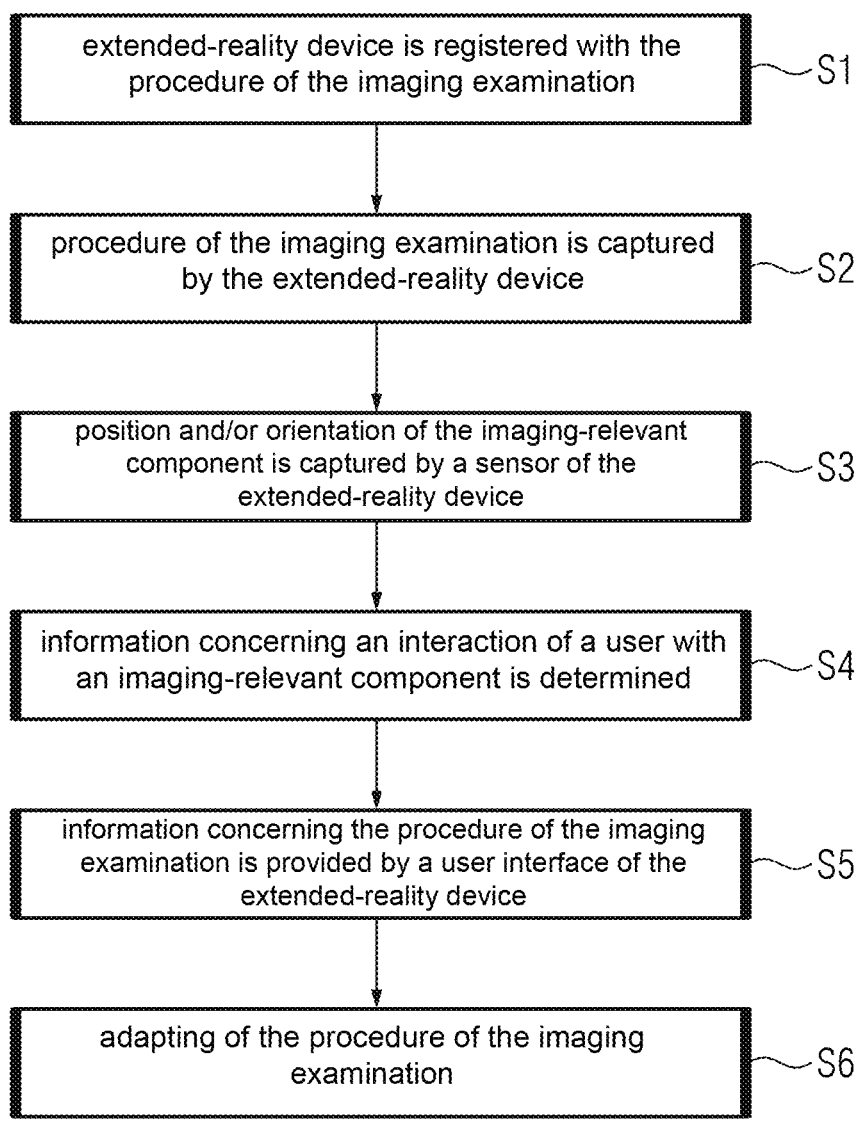

APPARATUS, SYSTEM AND METHOD FOR SUPPORTING A PROCEDURE OF AN IMAGING EXAMINATION

CROSS REFERENCE TO RELATED APPLICATIONS

This patent application claims priority to German Patent Application No. 10 2021 206 761.1, filed Jun. 29, 2022, which is incorporated herein by reference in its entirety.

BACKGROUND

Field

The disclosure relates to an extended-reality device comprising an interface, a computing unit and a user interface, said extended-reality device being configured to capture, by means of the interface, a procedure of an imaging examination using an imaging apparatus, and said computing unit being configured to determine information concerning the procedure of the imaging examination and to provide said information to a user of the extended-reality device by means of the user interface. The disclosure further relates to a system comprising an imaging apparatus with an extended-reality device, and to a method for providing information concerning a procedure of an imaging examination using a system comprising an imaging apparatus with an extended-reality device.

Related Art

Numerous steps are typically required when performing an imaging examination, and these steps must be monitored and executed by qualified and trained personnel. The environment of an imaging apparatus, for example a strong magnetic field or ionizing radiation, and the complex nature of the imaging process make it necessary in this case for the personnel to control the imaging apparatus from a separate control room while a patient who is to be examined remains inside the imaging apparatus in an examination space. This results in a physical distance between the personnel and the patient, which complicates interactions between the personnel and the patient and can hamper the preparation and/or performance of the imaging examination. Consequently, certain procedures of an imaging examination can be laborious and/or highly time-consuming.

In particular, procedures of the imaging examination which require the participation and/or coordination of a plurality of personnel can be challenging in this case. Examples include imaging examinations of (small) children and also surgical interventions and/or therapeutic measures which are accompanied by an imaging examination. In such cases, considerable effort will usually be required to prepare the patient, and also to coordinate the personnel (for example MTRAs, anesthetists, surgeons, radiologists, etc.). In the case of particularly complex interventions and/or significant participation of personnel members, it is also possible for errors and/or misunderstandings to occur which can jeopardize the execution of the imaging examination and also the safety of the patient. Therefore, use is typically made of standard operation protocols as well as runtime procedures or checklists, these being intended to ensure that an imaging examination is executed correctly. However, managing and/or following such checklists involves an additional effort and can further increase the effort that is required for the imaging examination.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 5 shows a flowchart of a method according to an exemplary embodiment of the disclosure.

Figure 1:
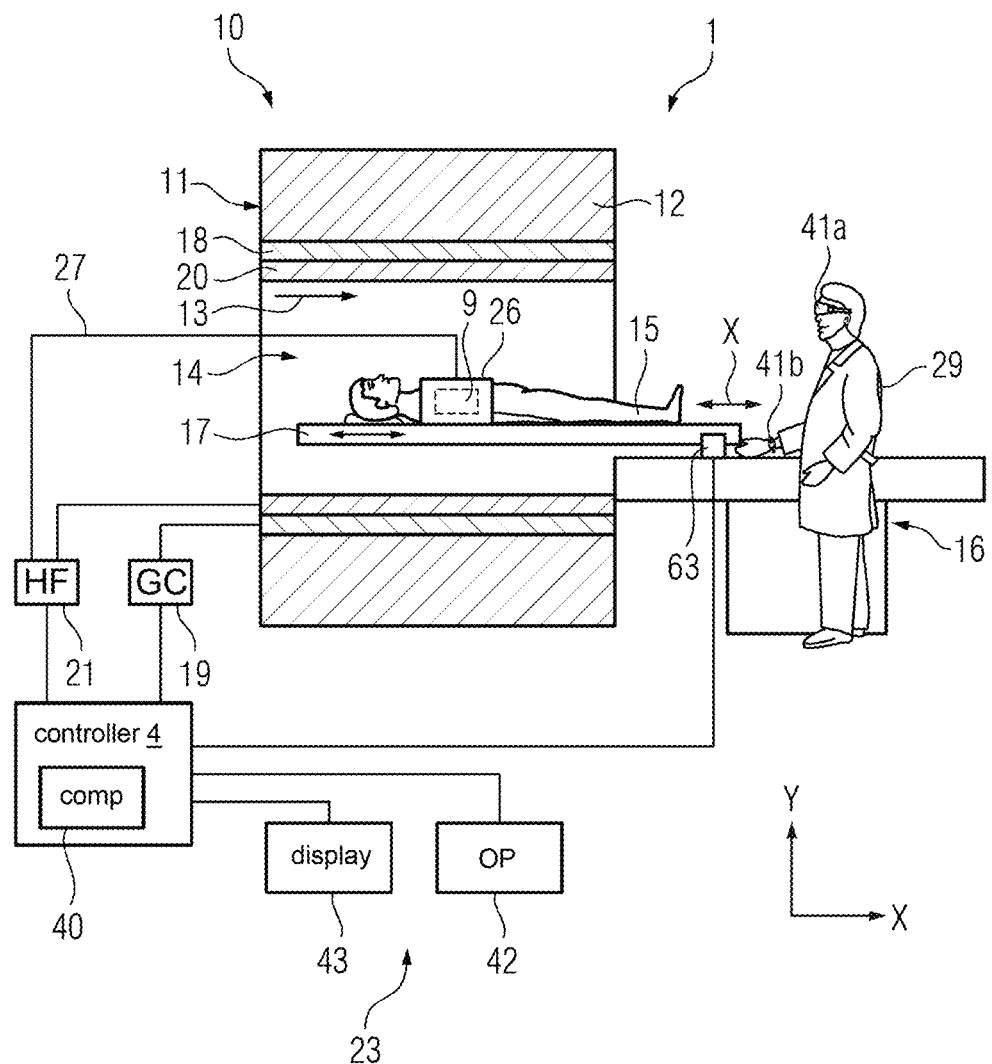
FIG. 1 shows a schematic representation of a system according to an exemplary embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is therefore to simplify the execution of an imaging examination and to reduce or prevent any occurrence of errors.

The inventive extended-reality device comprises an interface, a computing unit and a user interface, and is configured to capture, by means of the interface, a procedure of an imaging examination using an imaging apparatus, the computing unit being configured to determine information concerning the procedure of the imaging examination and to provide said information to a user of the extended-reality device by means of the user interface.

An imaging apparatus can be any medical device which is configured to capture image data relating to a body region of a patient. An imaging apparatus is preferably configured to record two-dimensional and/or three-dimensional image data, in particular time-dependent three-dimensional image data, of the body region of the patient. Examples of imaging apparatuses include magnetic resonance apparatuses, x-ray apparatuses, computer tomography systems, single-photon-emission computer tomography systems, positron-emission tomography systems, as well as mammography apparatuses, ultrasound devices, etc. In an exemplary embodiment, the imaging apparatus is embodied as a magnetic resonance apparatus.

An extended-reality device can be any device by means of which physical actions of a user are used as an entry or input for a digital data system. A physical action of the user can be, for example, a movement of a body region of the user, a gesture, an expression (facial expression), a touch command on an input interface, but also a noise or a voice input. The extended-reality device can be configured in particular to provide a three-dimensional space that can be used as an interface for visual, acoustic and/or haptic inputs and/or outputs. It is conceivable for the extended-reality device to use or provide "spatial computing" technology such as for example "virtual reality", "augmented reality" and/or "mixed reality" in order to allow interaction between the user and the extended-reality device. In particular, the extended-reality device can provide a user interface for interaction of the user with the imaging apparatus, said user interface being implemented by means of a "spatial computing" technology.

The interface, the computing unit and the user interface of the extended-reality device can be electrically and/or mechanically interconnected. The extended-reality device in this case is preferably configured as a mobile device which can be transported by the user. It is however equally conceivable for the interface, the computing unit and/or the user interface to be positioned at various locations in an examination space and/or to be able to be positioned variably relative to each other. For example, the user interface can be positioned on the user while the interface and/or the computing unit are electrically and/or mechanically connected to the imaging apparatus. In a further example, the interface and the user interface can be positioned on the user while the computing unit is connected to a computing unit of the imaging apparatus. It is further conceivable for the user interface to have a dedicated computing unit, in particular a GPU (graphics processing unit), which is configured for the purpose of processing image information. An interface can be configured as a communication interface, for example, but also as a sensor. For example, the sensor can be embodied as a camera, in particular a 2D camera or a 3D camera, which is configured to capture image data relating to an examination space of the imaging apparatus. The computing unit can be configured correspondingly to identify the procedure of the imaging examination as a function of the image data and to determine the information concerning the procedure of the imaging examination. It is however equally conceivable for information concerning the procedure of the imaging examination to be transmitted from the imaging apparatus to the interface of the extended-reality device by means of a signal connection. The interface, the computing unit and/or the user interface preferably have a signal connection which allows communication and/or an exchange of signals. Such a signal connection can be embodied in a wire-based or preferably wireless manner.

In an exemplary embodiment, the extended-reality device is embodied as data glasses or a virtual-reality headset. The extended-reality device can be configured in particular to output the information concerning the procedure of the imaging examination to the user visually and/or acoustically by means of the user interface. To this end, the user interface can have for example a projector, a visual display and/or a loudspeaker. The user interface can be configured in particular to implement spatial computing technology. The extended-reality device can however also be embodied as a smartwatch or other wearable smart device. A user interface can comprise for example a screen, a visual display, a projector, a loudspeaker or similar. It is also conceivable for the user interface to be configured to output the information concerning the procedure of the imaging examination to the user in a haptic manner, in particular by means of a force feedback.

The user interface is shaped according to a body region of the user and/or configured to be fastened mechanically to the body region of the user. The extended-reality device is preferably so embodied as to be wearable. This can mean that the extended-reality device is positioned and/or held on a body region of the user during a procedure of the imaging examination. It is however equally conceivable for only the user interface of the extended-reality device to be positioned on the body region of the user. The extended-reality device preferably has a fastening element which mechanically connects at least the user interface to the body region of the user. The extended-reality device and/or the user interface can be embodied as for example glasses, a headset, a glove or a watch which is fastened in an appropriate position to a head, arm and/or hand of the user. It is further conceivable for the extended-reality device to have a belt, a strap, an armband, a clamp, a clip or other fastening element which fastens at least the user interface to the body region of the user in a positive and/or non-positive manner. The fastening element can also mechanically connect the extended-reality device and/or the user interface to an item of clothing and/or part of an item of personal protective equipment of the user.

A user of the extended-reality device can be in particular a patient and/or a member of medical personnel such as for example a nurse, a doctor, a medical technical radiology assistant (MTRA), etc.

An imaging examination can be an imaging examination of a patient with the purpose of capturing images of a diagnostically relevant body region of the patient. An imaging examination can be in particular a procedure during which high-frequency electromagnetic waves are transmitted into an image recording region of the imaging apparatus, and high-frequency signals having a frequency and power range of normal magnetic resonance signals are captured from the image recording region. An imaging examination can also comprise a test and/or a calibration of the imaging apparatus, during which a phantom is positioned in the image recording region. The imaging examination preferably comprises all of the procedures and/or phases required to perform the imaging examination, in particular planning, preparation and performance of the imaging examination. The imaging examination can comprise one or more parameters, in particular imaging parameters, and/or one or more imaging sequences. An imaging parameter can be a boundary condition or a variable in an imaging sequence, by means of which it is possible to set the capture of image data for the diagnostically relevant body region of the patient.

A parameter of an imaging examination that is to be performed can be an imaging parameter, for example an image resolution, a contrast, a signal-to-noise ratio, a specific absorption rate, an echo time, a repetition time or similar. It is equally conceivable for the parameter to comprise a group of imaging parameters, an imaging sequence and/or a series of imaging sequences. Furthermore, a parameter can comprise any setting that relates to the imaging examination and/or execution of the imaging examination.

The imaging examination can also comprise one or more procedures. A procedure can be any section of the imaging examination. For example, a procedure can be positioning a patient table, positioning a patient, positioning a body region of the patient, positioning a local coil, starting an imaging sequence, registering the patient, an explanation to the patient, anesthesia, surgical intervention, a minimally invasive intervention, or similar. Information concerning the procedure of the imaging examination can relate to any parameter that is characteristic of or critical to the procedure of the imaging examination. The information concerning the procedure of the imaging examination can also define or initiate a user action that is dependent on the procedure. Examples of possible information concerning the procedure of the imaging examination include a positioning instruction for an imaging-relevant component and a representation of outstanding and/or completed steps of the imaging examination.

As a result of providing the inventive extended-reality device, procedures of the imaging examination can advantageously be performed and monitored more efficiently. Furthermore, errors in the planning, preparation and/or performance of the imaging examination can be identified and/or avoided more easily. It is thereby advantageously possible to reduce any risk to the patient, and also any risk of unsatisfactory image quality and/or repetition of the imaging examination.

By means of fastening the extended-reality device to a body region of the user, greater efficiency can advantageously be achieved in respect of user interaction with the imaging apparatus, control and/or monitoring of procedures of the imaging examination, and/or provision of information concerning the execution of the imaging examination.

According to an embodiment, the inventive extended-reality device has a sensor which is configured to capture a current position and/or orientation of an imaging-relevant component.

The sensor can be configured as an optical sensor in particular. For example, the sensor can comprise a 2D camera, a 3D camera, an infrared camera, but also a distance sensor such as for example a laser distance measuring device, an ultrasound sensor or similar. The extended-reality device can also have a plurality of sensors which are configured to capture the current position and/or orientation of the imaging-relevant component. The imaging-relevant component can be in particular an imaging apparatus, a patient table, a patient support apparatus, a local coil, a body region of a patient, a respiratory belt, a phantom or similar. It is equally conceivable for the imaging-relevant component to be any component that is required for a procedure of the imaging examination but exists separately from the imaging apparatus. For example, the imaging-relevant component can also be an ultrasonic sensor, a sound generator, a catheter, a medical instrument, an ECG device or similar.

In particular, a current position and/or orientation of the imaging-relevant component can refer to an absolute or relative distance and/or an alignment of the imaging-relevant component in relation to the imaging apparatus, the extended-reality device, the patient support apparatus, the patient table and/or the patient. It is however equally conceivable for the current position and/or orientation of the imaging-relevant component to refer to an absolute or relative distance and/or an alignment of a first imaging-relevant component in relation to a second imaging-relevant component.

The information concerning the procedure of the imaging examination relates in this case to an appropriate position and/or orientation of the imaging-relevant component. In an example, the information concerning the procedure of the imaging examination can comprise positional information such as for example a length dimension and/or a coordinate. It is however equally conceivable for the information concerning the procedure of the imaging examination to contain a positioning instruction for the positioning and/or alignment of the imaging-relevant component. Such a positioning instruction can include for example a directional indication, a directional instruction and/or a position display for the imaging-relevant component, and is output to the user by means of the user interface. Any other type of information concerning the procedure of the imaging examination is of course also conceivable.

The extended-reality device is configured to provide the information concerning the procedure of the imaging examination, by means of the user interface, in relation to the current position and/or orientation of the imaging-relevant component. For example, it is conceivable for the extended-reality device to be configured as data glasses by means of which the user can discern the current position and/or orientation of the imaging-relevant component, while the appropriate position and/or orientation of the imaging-relevant component is projected onto a viewing pane of the data glasses. It is however equally conceivable for the extended-reality device to be configured as a smartwatch which provides the user with a positioning instruction for the imaging-relevant component by means of a force feedback, an indicator on a display and/or an acoustic output. In addition to these, further variants of extended-reality devices, in particular virtual-reality headsets and/or augmented-reality devices, are of course conceivable.

As a result of providing the appropriate position and/or orientation of the imaging-relevant component in relation to the current position and/or orientation of the imaging-relevant component, it is advantageously possible to reduce or prevent errors in the positioning and/or alignment of the imaging-relevant component. Furthermore, as a result of providing the information concerning the procedure of the imaging examination by means of the extended-reality device, the user is able to position and/or align the imaging-relevant component in a particularly time-efficient manner.

In a further embodiment of the extended-reality device, the sensor is embodied as an optical sensor. The optical sensor can be embodied in particular as a 2D camera, a 3D camera or an infrared camera.

The optical sensor is configured to capture the position and/or orientation of the imaging-relevant component as a function of at least one optical marker. The at least one optical marker is preferably positioned on the imaging-relevant component and/or the extended-reality device. For example, the at least one optical marker can be positioned on the imaging-relevant component and captured by means of a camera which is mechanically connected to a VR headset or data glasses of the user. It is however equally conceivable for the camera of the extended-reality device to be mechanically connected to the imaging apparatus. In this case, the at least one optical marker can also be positioned on the user interface and/or on another component of the extended-reality device positioned on the user. It is further conceivable for both the imaging-relevant component and a component of the extended-reality device which is positioned on the user to each have at least one optical marker. The optical markers of the imaging-relevant components and of the extended-reality device preferably differ in respect of at least one attribute that can be captured by means of the optical sensor. In this case, the optical sensor which is configured to capture the at least one optical marker can be positioned at any location in an examination space.

The at least one optical marker can be configured to emit and/or reflect light in a predetermined frequency spectrum. To this end, the at least one optical marker can have a reflective material and/or an active light source such as for example an LED, an incandescent lamp or similar. It is equally conceivable for the optical marker to have a predetermined geometric shape such as for example a sphere, an oval, a polygon, a cone or similar, on the basis of which the optical marker can be captured and/or identified by means of the sensor.

The optical sensor is preferably configured to locate and/or capture the at least one optical marker in an examination space of the imaging apparatus. The optical sensor can be configured in particular to capture a light which is emitted or reflected by the at least one optical marker. It is however equally conceivable for the extended-reality device to have a light source which emits light in a predetermined frequency spectrum in a direction of the at least one optical marker. The at least one optical marker can then reflect the light in the predetermined spectrum, so that the optical sensor can capture the light that is reflected by the at least one optical marker.

The imaging apparatus and/or the imaging-relevant component preferably have a plurality of optical markers. The computing unit of the extended-reality device can be configured to determine an absolute position of the imaging apparatus and/or the imaging-relevant component, but also a relative position of the imaging apparatus and/or the imaging-relevant component in relation to the extended-reality device and/or a further imaging-relevant component on the basis of the plurality of optical markers. In particular, the computing unit is conceivably configured to identify a temporal course of the absolute and/or relative position of the imaging apparatus and/or imaging-relevant component on the basis of the at least one optical marker or the plurality of optical markers.

As a result of providing the optical sensor, greater accuracy is advantageously possible when capturing the position and/or orientation of the imaging apparatus and/or imaging-relevant component using at least one optical marker. Furthermore, different imaging-relevant components can advantageously be distinguished from each other by means of the extended-reality device when using different optical markers and/or a specific spatial arrangement of optical markers.

In a further embodiment, the at least one sensor is embodied as an acoustic sensor. In particular, the acoustic sensor can be embodied as a microphone which is configured to capture an utterance and/or a voice command of the user.

As a result of providing an acoustic sensor, the user is advantageously enabled to affect an input by means of a voice instruction and/or an acoustic noise. As a consequence, the user advantageously has their hands free to perform any procedures of the imaging examination which require manual interaction with the user.

According to an embodiment, the inventive extended-reality device has an input interface which is configured to capture an instruction from the user concerning an adaptation of the imaging examination. The input interface can allow an input from the user by means of one of the spatial computing technologies described above. For example, the input interface can be embodied as an acceleration sensor, a gyrosensor, a GPS receiver, an optical sensor, a location sensor, a distance sensor, a microphone, a controller or similar. Correspondingly, an input from the user can be inter alia a gesture, a movement, a voice control, an input on the controller, a movement of the controller or a facial expression of the user. In particular, the input from the user can be an instruction from the user for the purpose of adapting the imaging examination.

The extended-reality device can be configured to transfer the instruction from the user concerning the adaptation of the imaging examination to the imaging apparatus. To this end, the extended-reality device can have a signal connection to the imaging apparatus. The signal connection can be embodied in a wire-based or wireless manner. The extended-reality device is preferably connected to a controller and/or a computing unit of the imaging apparatus by means of the signal connection. In particular, the user interface of the extended-reality device can be connected to or integrated into a user interface and/or operating software of the imaging apparatus, so that the user can control the imaging apparatus by means of the input interface of the extended-reality device.

As a result of providing the input interface, the imaging apparatus can advantageously be operated remotely by means of the extended-reality device. As a consequence, contact between a member of the medical personnel and the patient during individual procedures of the imaging examination can advantageously be maintained, even if these procedures require a change to parameters of the imaging examination from a control room.

In a further embodiment, the inventive extended-reality device is also configured to provide information concerning an execution and/or a current status of the procedure of the imaging examination to the user by means of the user interface, and to receive an input from the user concerning the procedure of the imaging examination by means of an input interface.

The information concerning the execution and/or the current status of the procedure of the imaging examination can be in particular a display of progress and/or remaining duration of the imaging examination. It is equally conceivable for the information concerning the execution and/or the current status of the procedure of the imaging examination to comprise details of a current procedure from among a set of procedures of the imaging examination. For example, the information concerning the execution and/or the current status of the procedure of the imaging examination can comprise a progress bar and/or a time display which quantify the progress of a current procedure, for example positioning a local coil, administering an anesthetic, positioning the patient table, an imaging sequence, a respiratory phase or similar. In this case, the user can be in particular a patient who is informed about the execution and/or the current status of the procedure of the imaging examination by means of the extended-reality device. The input from the user can include inter alia selecting, by means of the input interface, any of the information cited above concerning the execution and/or the current status of the procedure of the imaging examination. The user interface is preferably configured to provide the user with an operating interface, in particular a graphical operating interface, which allows the user to make a corresponding selection.

In an exemplary embodiment, the extended-reality device is also configured to provide the patient with informative and/or entertaining content such as for example radio broadcasts, video content, audio content, but also visual and acoustic content with a calming effect. Furthermore, the extended-reality device is conceivably configured to allow communication between the patient and a member of the medical personnel. In a further embodiment, the user is one of a plurality of members of the medical personnel who are involved in the performance of the imaging examination. By means of the extended-reality device, the user can be informed of progress and/or the status of a procedure which is coordinated by another member of the medical personnel.

By means of the extended-reality device, a patient, and/or members of the medical personnel, can advantageously be informed about the current status of a procedure of the imaging examination. It is thereby possible advantageously to achieve greater efficiency when executing the imaging examination and/or to reassure and/or distract the patient during the execution of the imaging examination.

In an embodiment, the inventive extended-reality device is embodied as a virtual-reality headset which is configured to provide the user with a virtual environment by means of the user interface.

In an appropriate position for the purpose of the application, a virtual-reality headset can be positioned on the head of a user. The user interface of the virtual-reality headset preferably has two visual displays. The two visual displays can be arranged in such a way that each visual display is positioned in front of one eye of the user when the virtual-reality headset is appropriately positioned on the head of the user. It is conceivable for the digital environment displayed to the user to correspond to a real environment of the user, said real environment being captured by a camera of the virtual-reality headset and output by the user interface. In this case, the camera of the virtual-reality headset can be a sensor according to an embodiment described above.

It is further conceivable for the virtual environment to imitate a desired environment and/or to provide an artificial space. The virtual environment can distract the user, in particular a patient, from their position in an image recording region of the imaging apparatus. The virtual environment can moreover have a menu which allows navigation between various contents of the virtual environment. For example, it is conceivable for the virtual environment to include entertaining and/or informative content which informs the patient about a procedure of the imaging examination and/or prepares the patient for a procedure that will be performed during the imaging examination. The virtual environment can also be configured to increase the immersion of the user into the virtual environment in order to improve guidance of the user during the imaging examination.

As a result of providing the virtual environment, a patient can advantageously be distracted from their position in a narrow image recording region of an imaging apparatus. It is thereby possible to reduce any risk of interruption to the imaging examination in the case of patients having a nervous and/or claustrophobic disposition. As a result of the greater immersion of the patient into the virtual environment, it is moreover possible to improve patient cooperation in response to instructions and/or patient understanding of a procedure of the imaging examination.

The inventive system comprises an imaging apparatus with an extended-reality device according to an embodiment described above, said extended-reality device being configured to provide information, said information concerning a procedure of an imaging examination using the imaging apparatus, to a user by means of a user interface and to receive an input from the user, concerning the procedure of the imaging examination, by means of an input interface.

The imaging apparatus of the system can be embodied in accordance with an embodiment described above. It is further conceivable for the imaging apparatus to have a signal connection to the extended-reality device in order to allow an exchange of data between the imaging apparatus and the extended-reality device. Such data can comprise for example parameters of the imaging examination, control commands for controlling the imaging apparatus, but also data captured by the sensor of the extended-reality device. It is conceivable for the input from the user to include an adaptation of a parameter of the imaging examination, but also a selection of information concerning the imaging examination procedure and/or information concerning a patient.

As a result of providing a system according to the disclosure, it is possible to provide a predetermined system structure and/or a predetermined relative position of imaging-relevant components. It is therefore possible advantageously to simplify registration of the imaging apparatus and/or imaging-relevant components with the extended-reality device. By virtue of the system structure, it is moreover possible to simplify and/or optimize a communication infrastructure and/or an exchange of information between the imaging apparatus and the extended-reality device. It is therefore possible advantageously to reduce the time required to transfer and/or process data. It is further conceivable for a member of the medical personnel to control the imaging apparatus by means of the input interface of the extended-reality device, whereby spatial separation of the patient from the member of the medical personnel is advantageously avoided.

In an embodiment, the inventive system comprises a plurality of extended-reality devices, wherein a computing unit of a first extended-reality device is configured to determine information concerning a task of a first user and to provide said information to a second user by means of a second extended-reality device, wherein the information which is provided to the second user and concerns the task of the first user differs from information which concerns the procedure of the imaging examination and is provided to the first user by means of the user interface of the first extended-reality device.

It is conceivable for a plurality of users (for example members of the medical personnel) to monitor and/or manage different procedures of the imaging examination. It is further conceivable for a plurality of procedures of the imaging examination to be based on each other and/or reciprocally dependent. In particular, it may be necessary for the members of the medical personnel to synchronize and/or coordinate individual procedures. Examples of this include individual steps of an assisted surgical intervention, for example marking an incision, disinfecting a body region of the patient, preparing medical instruments, positioning the patient, anaesthetizing the patient, logging medical instruments after the intervention, etc.

The information which is provided to the second user and concerns the task of the first user can include in particular the current task status, task progress, outcome of the task, quantification of the success of the task, etc.

As a result of providing the information concerning the task of a first user, it is advantageously possible for at least one second user to monitor and/or track procedures of the imaging examination. It is thereby possible advantageously to avoid errors when performing the imaging examination. Furthermore, it is possible advantageously to increase the efficiency of the execution of the imaging examination by informing a plurality of members of the medical personnel, since for example individual procedures can be synchronized and/or coordinated more effectively.

The inventive method for providing information concerning a procedure of an imaging examination, said examination using a system comprising an imaging apparatus with an extended-reality device as per an embodiment described above, comprises the following steps: capturing the procedure of the imaging examination by means of an interface of the extended-reality device, determining information concerning an interaction of a user with an imaging-relevant component, as a function of the procedure of the imaging examination, by means of a computing unit of the extended-reality device, providing the information concerning the procedure of the imaging examination, as a function of the determined information concerning the interaction of the user with the imaging-relevant component, by means of a user interface of the extended-reality device.

The interface of the extended-reality device can be configured to request information concerning the procedure of the imaging examination from the imaging apparatus by means of a signal connection. In this case, the signal connection can be embodied in a wire-based or wireless manner. For example, the extended-reality device can request a status and/or progress of the procedure of the imaging examination from the imaging apparatus at discrete time intervals by means of the interface. The extended-reality device can also be configured to capture an input from a user by means of an input interface in order to determine a procedure and/or a series of procedures of the imaging examination as a function of the input from the user. Furthermore, the extended-reality device can be configured to identify an action of a user and to determine the procedure of the imaging examination on the basis of the action. In this case, the identification of the action of the user can be affected in particular by means of a sensor of the extended-reality device. It is further conceivable for the user to input the procedure of the imaging examination by means of the input interface of the extended-reality device. The extended-reality device can be synchronized with the respective procedure of the imaging examination in this way. In particular, the extended-reality device can have a computing unit and/or a controller which coordinates or implements the capture of the procedure of the imaging examination.

The determination of the information concerning the interaction of the user with the imaging-relevant component can be affected in particular as a function of an input and/or an identified action of the user. It is however equally conceivable for the information concerning the interaction of the user with the imaging-relevant component to be transmitted from the imaging apparatus to the extended-reality device by means of the signal connection. The information concerning the interaction of the user with the imaging-relevant component can relate in particular to a current position and/or orientation of an imaging-relevant component such as for example a body region of a patient and/or a local coil of a magnetic resonance apparatus. The information concerning the interaction of the user with the imaging-relevant component is preferably determined by means of a computing unit of the extended-reality device and/or of the imaging apparatus.

The information concerning the interaction of the user with the imaging-relevant component can include, for example, a current and/or future action of the user in relation to the imaging-relevant component. The computing unit can determine the current and/or future action of the user on the basis of data that is captured by the sensor and/or the interface of the extended-reality device. In this context, the sensor can be embodied in particular as a camera which captures image data from the examination space of the imaging apparatus. It is equally conceivable for the computing unit to determine the information concerning the interaction of the user with the imaging-relevant component on the basis of data from other sensors or a plurality of sensors. In an embodiment, in order to determine the information concerning the interaction of the user with the imaging-relevant component, information from a database of the imaging apparatus is processed, said database being used to store information concerning the procedures of the imaging examination or a plurality of imaging examinations. It is conceivable for the computing unit of the extended-reality device and/or of the imaging apparatus to process both data from the sensor and information from the database of the imaging unit in order to determine the information concerning the interaction of the user with the imaging-relevant component.

The information concerning the procedure of the imaging examination preferably comprises an instruction concerning the appropriate positioning and/or alignment of the imaging-relevant component. The instruction concerning the appropriate positioning and/or alignment of the imaging-relevant component can be provided, in particular in relation to a current position and/or orientation of the imaging-relevant component, by means of the user interface of the extended-reality device. In this case, the extended-reality device can be embodied as data glasses with a viewing pane which allows the user to see the imaging-relevant component. It is conceivable for the information concerning the procedure of the imaging examination to be projected onto the viewing pane of the data glasses in order to provide the user with the instruction concerning the appropriate positioning and/or alignment of the imaging-relevant component. The information concerning the procedure of the imaging examination can of course also comprise other information or further information as described above concerning the procedure of the imaging examination.

In an embodiment, the information concerning the procedure of the imaging examination is provided to the user by means of a virtual-reality headset. In this context, image data from the examination space, said data being recorded by means of the sensor of the extended-reality device, can be provided to the user on a display of the virtual-reality headset. The image data can essentially be provided to the user in real time. It is further conceivable for the user interface of the extended-reality device to provide the user with an operating interface of the imaging apparatus. Said operating interface can allow the user to interact with and/or control the imaging apparatus.

The inventive method advantageously allows the imaging apparatus to be controlled and/or monitored by a user in a time-efficient manner.

According to an embodiment, the inventive method additionally comprises the step: registering the extended-reality device with the procedure of the imaging examination, wherein said registration comprises capturing registration information by means of a sensor of the extended-reality device, and synchronizing the extended-reality device with the imaging apparatus and/or an imaging-relevant component as a function of the registration information.

The registration of the extended-reality device with the procedure of the imaging examination can involve in particular a calibration of the extended-reality device. In this context, a coordinate system of an image space which is captured by the at least one sensor can be matched and/or synchronized with a coordinate system of the imaging apparatus. The sensor of the extended-reality device is preferably embodied as a camera in this case. In an embodiment, use is made of a known or predetermined arrangement of optical markers which are positioned on the imaging apparatus and/or an imaging-relevant component. The arrangement of optical markers can be captured accordingly by means of the sensor, and a geometric arrangement of the imaging apparatus in relation to an imaging-relevant component can be identified. It is equally conceivable to determine a relative position and/or a relative alignment of the extended-reality device in relation to the imaging apparatus and/or the imaging-relevant component as a function of the arrangement of optical markers. The arrangement of optical markers can characterize in particular a geometric arrangement of the imaging apparatus and/or imaging-relevant component, and/or indicate the presence of an imaging-relevant component.

It is conceivable for the registration of the extended-reality device with the procedure of the imaging examination to include an analysis and/or identification of imaging-relevant components which are involved in the procedure of the imaging examination and/or taken into consideration when executing the procedure of the imaging examination.

The capture of the registration information by means of the sensor of the extended-reality device can include in particular the capture of a spatial location, a spatial arrangement and/or a code or registration number of the imaging apparatus and/or of an imaging-relevant component. The sensor of the extended-reality device is preferably configured to scan or capture the registration information by optical means. It is conceivable for the registration information to be linked with information concerning possible procedures of the imaging examination and/or the presence of an imaging-relevant component.

The extended-reality device is synchronized with the imaging apparatus and/or the imaging-relevant component as a function of the registration information. In this case, in particular a program, a user interface, a coordinate system, a graphical operating interface or an output of the extended-reality device can be adapted to a state of the imaging apparatus, a type and/or number of imaging-relevant components or an imaging examination that is to be performed. In this case, the coordinate system can be used in particular to implement spatial computing as per an embodiment described above.

The registration of the extended-reality device with the procedure of the imaging examination can be in particular a substep of the capture of the procedure of the imaging examination.

As a result of registering the extended-reality device with the procedure of the imaging examination, greater accuracy can advantageously be achieved when identifying the relative position of the extended-reality device in relation to the imaging apparatus and/or the imaging-relevant component. Furthermore, by means of the registration, a program and/or a graphical operating interface of the extended-reality device can automatically be adapted to the imaging examination to be performed and/or the procedure of the imaging examination.

In a further embodiment, the inventive method comprises the step:
capturing a current position and/or orientation of the imaging-relevant component by means of a sensor of the extended-reality device, wherein the determination of the information concerning the interaction of the user with the imaging-relevant component is affected as a function of the current position and/or orientation of the imaging-relevant component.

The sensor of the extended-reality device can be embodied as per an embodiment described above as a camera which is configured to capture a current position and/or orientation of the imaging-relevant component or of a plurality of imaging-relevant components. It is conceivable for a computing unit of the extended-reality device and/or of the imaging apparatus to determine the information concerning the interaction of the user with the imaging-relevant component as a function of the current position and/or orientation of the imaging-relevant component. The information concerning the interaction of the user with the imaging-relevant component can be updated at discrete time intervals in this case. A time interval for updating the information concerning the interaction of the user with the imaging-relevant component can correspond to, or be a multiple of, a time interval for the capture of image data by means of the camera. It is however also conceivable for an update of the information concerning the interaction of the user with the imaging-relevant component to be executed at a time point following a performance of the procedure of the imaging examination.

In an embodiment, the capture of the current position and/or orientation of the imaging-relevant component can include capturing a plug-to-socket arrangement of an electrical connection between a local coil and an input channel of a magnetic resonance apparatus. In this case, the determination of the information concerning the interaction of the user with the imaging-relevant component take place as a function of data from a database, which database contains information concerning the correct electrical connection of the local coil to the input channel of the magnetic resonance apparatus for a plurality of imaging examinations and/or arrangements of local coils. The information concerning the interaction of the user with the imaging-relevant component can include, for example, an instruction to a user concerning an optimized electrical connection of the local coil to the magnetic resonance apparatus. In this context, correct pairings of plugs and sockets, these being for example color-coded and/or identified by a marker, can be output to the user by means of the user interface as information concerning the procedure of the imaging examination. It is equally conceivable for incorrect and/or inefficient pairings of plugs and sockets to be indicated to the user by means of a colored or geometric marking.

The imaging-relevant component in this case comprises at least a body region of a patient, a component of the imaging apparatus and/or a device that is relevant for the imaging examination. A device that is relevant for the imaging examination can be in particular a device that is diagnostically or therapeutically relevant, but also a device for monitoring the patient. The device that is relevant for the imaging examination can also be a medical instrument which is suitable for an invasive or minimally invasive intervention.

As a result of providing the information concerning the procedure of the imaging examination, it is advantageously also possible to guide a user who is performing or coordinating the procedure of the imaging examination without sufficient expert knowledge and/or experience. It is therefore possible in an emergency situation for even unqualified personnel to perform individual procedures of the imaging examination.

In an exemplary embodiment of the inventive method, the determination of the information concerning the interaction of the user with the imaging-relevant component includes identifying a variance between the current position and/or orientation of the imaging-relevant component and an appropriate position and/or orientation of the imaging-relevant component, said variance being output to the user when the information concerning the procedure of the imaging examination is provided.

The variance of the current position and/or orientation of the imaging-relevant component from the appropriate position and/or orientation of the imaging-relevant component is preferably determined by the computing unit of the extended-reality device and/or of the imaging apparatus. In this case, the determination of the variance can take place as a function of data that is captured by the sensor of the extended-reality device together with information concerning the imaging examination from a database. On the basis of the variance, the computing unit preferably specifies a positioning instruction for the imaging-relevant component, said instruction being output to the user by means of the user interface as information concerning the procedure of the imaging examination. In this case, the positioning instruction can be a directional indication, a directional instruction, a coordinate, a schematic representation of the imaging-relevant component in the appropriate position and/or orientation (for example in the form of a schematic diagram) or similar. It is further conceivable for the computing unit to update the positioning instruction as a function of a time interval of the data capture by means of the sensor of the extended-reality device.

In addition to an embodiment described above, an imaging-relevant component can be in particular a phantom, a phantom local coil arrangement, a local coil, a patient, a body region of the patient, a respiratory belt, a sensor or wire of an ECG device, a patient support apparatus, a patient table, etc. An imaging-relevant component can also be any device which is suitable for monitoring the patient and/or a medical parameter of the patient (for example blood level, oxygen saturation, temperature, heart signals, respiration, pulse, etc.). In an exemplary embodiment, the extended-reality device is embodied as data glasses or a virtual-reality headset. In the case of data glasses, the positioning instruction can be projected onto a surface of a viewing pane, while in the case of a virtual-reality headset the positioning instruction can be shown by means of a visual display.

By repeatedly determining the variance between the appropriate position and/or orientation of the imaging-relevant component and the current position and/or orientation of the imaging-relevant component, it is possible advantageously to increase the quality of guidance given to the user during the procedure of the imaging examination. It is thereby possible in particular to perform the procedure of the imaging examination in a more time-efficient manner, but also to avoid errors in the positioning and/or alignment of imaging-relevant components.

In an embodiment of the inventive method, the user is a patient, wherein the determination of the information concerning the interaction of the user with the imaging-relevant component comprises determining an instruction to the patient as a function of the procedure of the imaging examination, and wherein the instruction to the patient comprises at least a respiration instruction and/or guidance for positioning at least a body region of the patient.

It is conceivable for the extended-reality device to be synchronized with an imaging sequence of the imaging apparatus by means of the signal connection to the imaging apparatus. This means that the extended-reality device can capture or determine progress of the procedure of the imaging sequence. The determination of the instruction to the patient is preferably affected as a function of the progress of the imaging sequence. The extended-reality device can therefore control and/or coordinate the instruction to the patient relative to time as a function of the progress of the imaging sequence. The instruction to the patient can be for example a respiration instruction, whereby a patient is requested to hold their breath for a short time while a diagnostic image of the patient is recorded by means of the imaging apparatus. It is equally conceivable for the instruction to be a request to reposition at least a body region of the patient, in order to capture a diagnostic image of this body region or a further body region by means of the imaging apparatus.

The information concerning the interaction of the patient with the imaging-relevant component is preferably determined by means of the computing unit of the extended-reality device and/or of the imaging apparatus as a function of the progress of the procedure of the imaging examination. The provision of the information concerning the procedure of the imaging examination can include in particular an output of the instruction to the patient. The output of the instruction to the patient is affected acoustically and/or visually by means of a projection, a display on a visual display, an output from a loudspeaker, or similar. In an exemplary embodiment, the provision of the instruction to the patient is affected by means of a visual display of a virtual-reality headset. In particular, the instruction to the patient in this case can be embedded in a virtual environment which aids or increases the immersion of the patient.

As a result of using a virtual-reality device according to the disclosure, patient concentration can advantageously focus on the performance of an action that is associated with the instruction. It is thereby possible to improve the cooperation and/or assistance of the patient during the imaging examination, as well as the quality of recorded image data.

In a further embodiment of the inventive method, the provision of information concerning the procedure of the imaging examination includes the provision of information concerning progress and/or a current status of the procedure of the imaging examination.

The information concerning the progress and/or the current status of the procedure of the imaging examination can include a graphical element such as for example a progress bar, a counter, a clock or similar, which is provided to the user on a display unit of the extended-reality device. It is equally conceivable for the information concerning the progress and/or the current status of the procedure of the imaging examination to include information concerning an imaging parameter, an imaging sequence, a section of an imaging sequence, a number of outstanding and/or completed imaging sequences, and also a number of outstanding and/or completed procedures of the imaging examination. The information concerning the progress and/or current status of the procedure of the imaging examination can also include information concerning the status of the procedure of the imaging examination and a member of the medical personnel assigned to the procedure. In an exemplary embodiment, the information concerning the progress and/or the current status of the procedure of the imaging examination includes a list-type representation of outstanding and/or completed procedures of the imaging examination. Completed and outstanding procedures of the imaging examination can be marked differently in this case, allowing the user to identify the status of the imaging examination in a time-efficient manner.

In an embodiment, the extended-reality device has a plurality of cameras which capture image data relating to an environment of the user and/or relating to the user. In this case, at least one camera of the extended-reality device can be directed at a facial region of the user, in order to capture a facial expression and/or an eye movement of the user. In particular, it is conceivable for a captured facial expression and/or eye movement of the user to be used for the purpose of determining an imaging-relevant component observed by the user and/or determining a navigation of the user in the virtual menu. The user interface of the extended-reality device can provide the user with a virtual menu and/or information which relates to an adaptation of the imaging-relevant component, but also to a current status of a procedure of the imaging examination, said procedure being dependent on the imaging-relevant component.

As a result of providing the information concerning progress and/or a current status of the procedure of the imaging examination, it is possible advantageously to improve the organization and/or time management of an imaging examination. Furthermore, errors or problems when performing the procedure of the imaging examination can be recognized and rectified promptly. In particular, it is conceivable for the user to be a patient who is informed about the current progress and/or status of a procedure of the imaging examination by means of the extended-reality device. It is thereby possible to answer questions from the patient during the imaging examination and/or advantageously to avoid interruption by the patient of activities of a member of the medical personnel.

According to an embodiment, the inventive method additionally comprises the step: receiving an instruction concerning an adaptation of the procedure of the imaging examination by means of an input interface of the extended-reality device, wherein the adaptation of the procedure of the imaging examination comprises at least an adaptation of a parameter of the imaging examination, an imaging sequence and/or a parameter of an imaging sequence.

The input interface can be embodied as part of the user interface of the extended-reality device and/or as part of the sensor of the extended-reality device. It is conceivable for the sensor to be configured as a camera which is configured as part of the user interface and/or input interface of the extended-reality device. For example, the camera can capture a movement of the user and transmit said movement to the computing unit of the extended-reality device. The captured movement can be a gesture, a facial expression and/or any desired movement which encodes an input for the extended-reality device and/or the imaging apparatus. For example, the user interface can be configured to provide the user with a virtual menu by means of a spatial computing technology, said menu allowing adaptation of a procedure of the imaging examination. In this case, the adaptation of the imaging apparatus can be affected by means of gesture control in particular, gestures of the user being captured by means of the camera of the extended-reality device.

A parameter of the imaging examination can comprise in particular an imaging parameter of an imaging sequence. It is however equally conceivable for a parameter of the imaging examination to be a position and/or an orientation of an imaging-relevant component. In particular, the imaging-relevant component can have a motor or drive by means of which the imaging-relevant component can be remotely controlled and/or automatically positioned and/or aligned. Examples of such components include a patient support apparatus, a patient table, a radiation filter, a radiation screen, a collimator, a radiation detector, a radiation emitter, a positioning aid for medical instruments (for example needles, catheter, etc.) and the like.

As a result of being able to adapt the procedure of the imaging examination by means of the extended-reality device, it is advantageously possible to avoid the need for the user to leave the examination space. This means that the user can advantageously maintain contact with the patient during the procedure of the imaging examination. Furthermore, it is advantageously possible to avoid the user repeatedly entering and leaving the examination space for various and/or consecutive procedures of the imaging examination, whereby the duration of the imaging examination can be reduced. It is further conceivable for qualified personnel, for example a radiologist, personally to be positioned in an image recording region of the imaging apparatus as a patient and to coordinate and/or control an imaging examination by means of the extended-reality device.

FIG. 1 shows an embodiment variant in which the imaging apparatus 10 of the inventive system 1 is embodied as a magnetic resonance apparatus 10. The magnetic resonance apparatus 10 in this case has a magnet unit 11 which comprises for example a permanent magnet, an electromagnet or a superconductive main magnet 12 for generating a strong and in particular homogeneous main magnetic field 13. The magnetic resonance apparatus 10 additionally comprises a patient receiving region 14 for receiving a patient 15. The patient receiving region 14 is cylindrical in the present exemplary embodiment and is surrounded circumferentially by the magnet unit 11. Designs of the patient receiving region 14 which vary from this example are however also conceivable in principle.

The patient 15 can be positioned in the patient receiving region 14 by means of a patient support apparatus 16 of the magnetic resonance apparatus 10. To this end, the patient support apparatus 16 has a patient table 17 which can be moved within the patient receiving region 14. The magnet unit 11 also has a gradient coil 18 for generating magnetic field gradients which are used for spatial encoding during imaging. The gradient coil 18 is triggered by means of a gradient controller 19 of the magnetic resonance apparatus 10. The magnet unit 11 can further comprise a high-frequency antenna which, in the present exemplary embodiment, is configured as a body coil 20 that is permanently integrated in the magnetic resonance apparatus 10. The body coil 20 is configured to excite the atomic nuclei that are located in the main magnetic field 13 generated by the main magnet 12. The body coil 20 is triggered by a high-frequency unit 21 of the magnetic resonance apparatus 10 and beams high-frequency signals into an image recording region, which is essentially formed by a patient receiving region 14 of the magnetic resonance apparatus 10. The body coil 20 can additionally be configured to receive magnetic resonance signals of the patient 15.

For the purpose of controlling the main magnet 12, the gradient controller 19 and the high-frequency unit (frequency controller) 21, the magnetic resonance apparatus 10 has a controller 4. The controller 4 is configured to monitor the performance of a sequence such as for example an imaging gradient-echo sequence or a turbo-spin-echo sequence. In an exemplary embodiment, the controller 4 (and/or one or more components therein) includes processing circuitry that is configured to perform one or more respective functions and/or operations of the controller 4 (and/or component(s) therein). In the example shown, the controller 4 also comprises a computing unit 40 which is configured to evaluate magnetic resonance signals that are captured during the imaging examination. In an exemplary embodiment, the computing unit 40 includes processing circuitry that is configured to perform one or more respective functions and/or operations of the computing unit 40. For example, the computing unit 40 may include one or more processors. The computing unit 40 may include one or more memory units and/or may be configured to access one or more external memory units.

The computing unit 40 and/or the controller 4 can additionally be configured to process data which is captured by means of a sensor of the extended-reality device 41 and/or a sensor 63 of the imaging apparatus 10, and which is transmitted to the computing unit 40 and/or the controller 4 by means of a wireless signal connection. In the example shown, the user 29 is a radiologist who is wearing data glasses 41a and a smartwatch 41b as extended-reality devices 41.

A computing unit of the extended-reality device 41 and/or the computing unit 40 of the imaging apparatus 10 are configured in particular to determine a position and/or orientation for an imaging-relevant component. The imaging-relevant component in the present example is represented by the patient table 17, the local coil 26 and/or a body region of the patient 15. The position and/or orientation of the imaging-relevant component is preferably identified as a function of a current procedure of an imaging examination and/or as a function of a current position and/or orientation of the imaging-relevant component which is captured by means of the sensor of the extended-reality device 41. The position and/or orientation of the imaging-relevant component is preferably output to the user 29 by means of a user interface 44 (see FIG. 4) of the extended-reality device 41. It is conceivable, for example, for the smartwatch 41b to output a positioning instruction to the user 29 by means of force feedback (for example a vibration pulse) and/or a visual display. The computing unit 40 of the magnetic resonance apparatus 10 and/or the computing unit of the extended-reality device 41 can be configured to specify and exchange, by means of a wireless signal connection, the positioning instruction described above.

As shown in FIG. 1, the magnetic resonance apparatus 10 can have a sensor 63 which captures the current position of the patient table 17 as a function of its displacement relative to the patient support apparatus 16. The sensor 63 can be embodied as a position pick-up, for example, and have an interface for transferring the information concerning the current position of the patient table 17 to the computing unit 40 and/or the controller 4 in a wireless or wire-based manner By combining data from a camera of the data glasses 41a and data from the position pick-up 63, the accuracy with which the current position of the patient table 17 is identified and therefore the accuracy with which the positioning instruction is specified can be increased in comparison with a positioning instruction which is based solely on image processing using image data from the camera of the extended-reality device 41.

The magnetic resonance apparatus 10 further comprises a stationary user interface 23 which is located in a separate control room (not shown) and has a signal connection to the controller 4. The display 43 of the stationary user interface 23 is preferably embodied as a monitor which is configured to display medical image data relating to the target region 9 of the patient 15 to the user 29. It is equally conceivable for the display 43 to have a graphical operating interface for setting imaging parameters of the magnetic resonance apparatus 10. The stationary user interface 23 can additionally have an operating unit 42 by means of which the user 29 can adapt parameter sets of the magnetic resonance apparatus 10. The operating unit 42 may be a human-machine interface, such as an input-output interface. The operating unit 42 can include, for example, a keyboard, mouse, microphone, or other input device. The stationary user interface 23 can also provide options for starting, stopping and/or parameterizing the inventive method.

Figure 4:
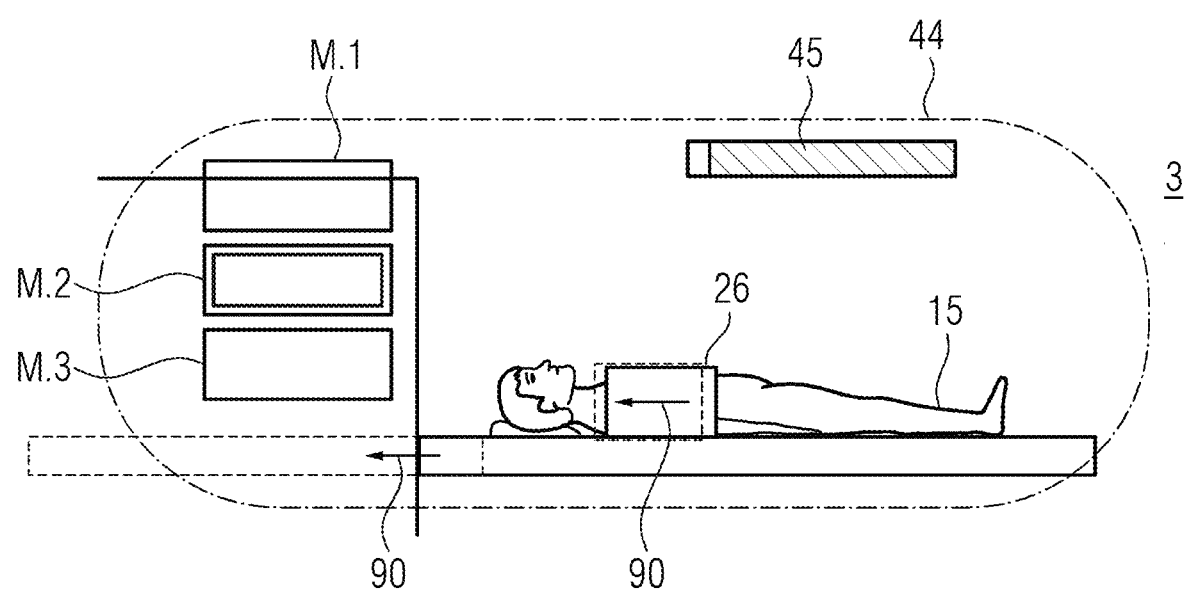
FIG. 4 shows a schematic representation of an extended-reality device according to an exemplary embodiment of the disclosure.

In an exemplary embodiment variant, the extended-reality device 41 is coupled to the stationary user interface 23 of the magnetic resonance apparatus 10. The extended-reality device 41 can be configured correspondingly to execute a functionality of the stationary user interface 23 and/or to capture information which is provided by means of the stationary user interface 23. For example, a projector of the data glasses 41a can be configured to provide a graphical operating interface of the stationary user interface 23 on a viewing pane of the data glasses 41a. The user interface 44 of the data glasses 41a can additionally be configured to accept an input from the user 29. In this case, the input from the user 29 can comprise in particular an adaptation of an imaging parameter and/or imaging sequence of the imaging examination. Of course, the user interface 44 of the data glasses 41a can also be configured to provide the user 29 with a positioning instruction for the imaging-relevant component, as shown in FIG. 4.

The magnetic resonance apparatus 10 further comprises a local coil 26 which is positioned on the target region 9 of the patient 15 and captures magnetic resonance signals from the target region 9 of the patient 15. The local coil 26 here has an electrical connection cable 27 which provides a signal connection to corresponding input channels of the high-frequency unit 21 and the controller 4. The input channels filter and digitize the signals received from the local coil 26 and transfer the data to the computing unit 40, which derives an image or a spectrum from the data and provides this to the user 29 of the imaging apparatus via the display unit 41c. In an embodiment variant, the extended-reality device is configured to provide a positioning instruction for a plug/socket arrangement of a number of local coils 26 and a number of input channels of the imaging apparatus 10. The user 29 is therefore guided to affect a correct and/or as far as possible efficient electrical connection of the number of local coils 26 to the number of input channels of the imaging apparatus 10.

Figure 2:
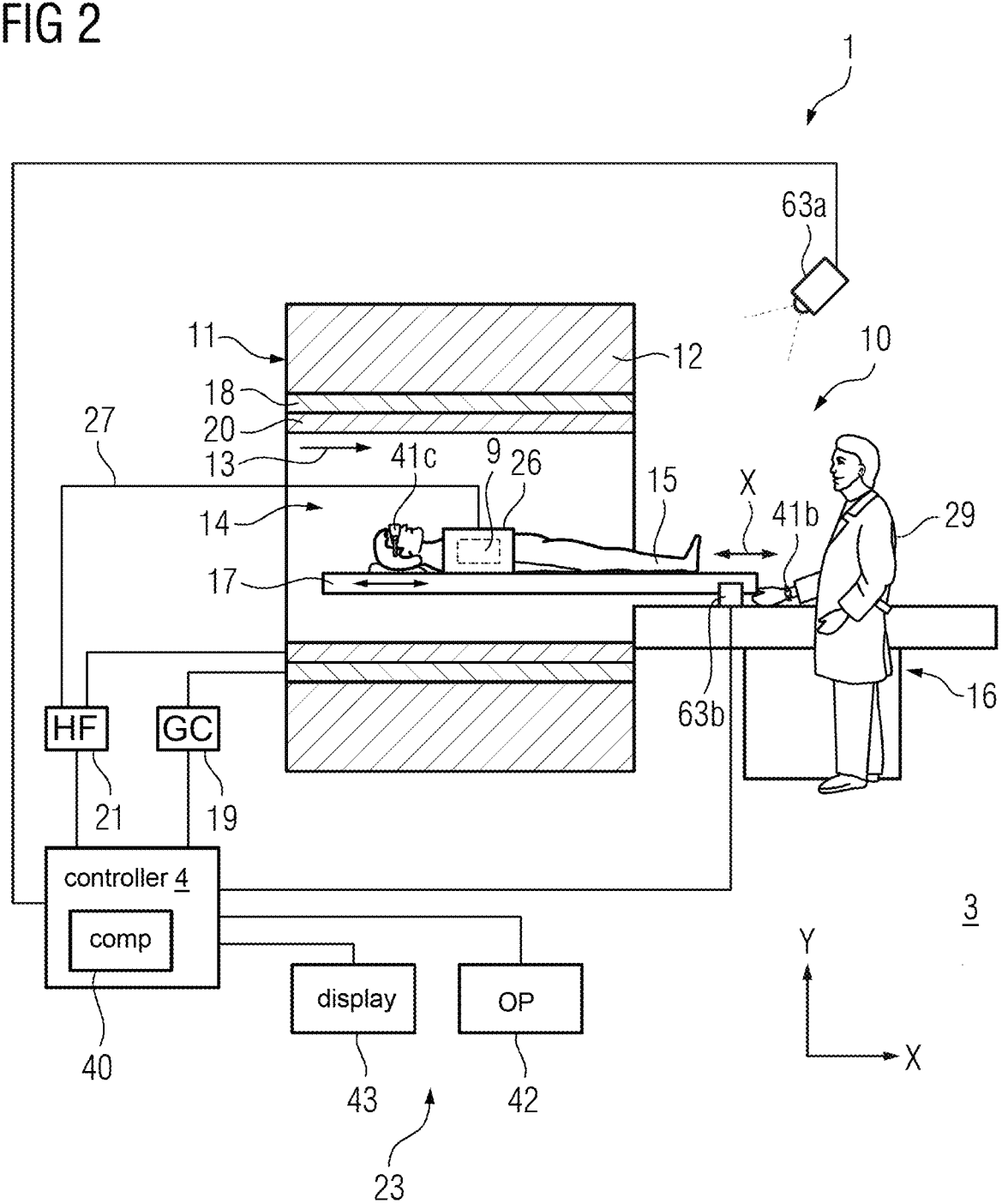
FIG. 2 shows a schematic representation of a system according to an exemplary embodiment of the disclosure.

FIG. 2 shows an embodiment variant in which the magnetic resonance apparatus 10 of the inventive system 1 has a camera 63a for capturing a current position and/or orientation of an imaging-relevant component. It is conceivable for image data that is captured by the camera 63a to be transferred via a signal connection to the computing unit 40 of the magnetic resonance apparatus 10 and/or to a computing unit of the smartwatch 41b. As a function of the image data that is captured by the camera 63a, it is possible to identify a variance of a current position and/or orientation of the imaging-relevant component from an appropriate position and/or orientation of the imaging-relevant component. A positioning instruction is determined on the basis of the variance and is output to the user 29 by means of for example a visual display and/or force feedback of the smartwatch 41b. The user 29 is then able to move the patient table 17 shown to an appropriate position. The appropriate position of the patient table 17 can be characterized by a positioning of the target region 9 of the patient 15 in an imaging volume, in particular an isocenter, of the magnetic resonance apparatus 10.

It is further conceivable for the patient 15 to be a user 29 of the extended-reality device 41. The extended-reality device 41c can be configured in particular to provide the patient 15 with respiration instructions and/or information concerning progress and/or a current status of the procedure of the imaging examination. Furthermore, the extended-reality device 41c can be configured to allow communication with a member of the medical personnel, in particular a further user 29 of an extended-reality device 41. In an embodiment variant, the extended-reality device 41 is embodied as a virtual-reality headset 41c which provides the patient 15 with a virtual environment that distracts the patient 15 from the surroundings of the image recording region.

In an embodiment variant of the inventive system 1, the system 1 also has a projector (not shown) which is configured to project information concerning the imaging procedure onto an imaging-relevant component in the examination space 3. For example, the projector can be configured to project information concerning a position and/or orientation of a local coil, an incision location for a surgeon, an insertion point for a catheter or also a needle or similar, onto a surface of a patient. It is conceivable for the sensor of the extended-reality device to be configured to capture and process the projection of the projector.

Figure 3:
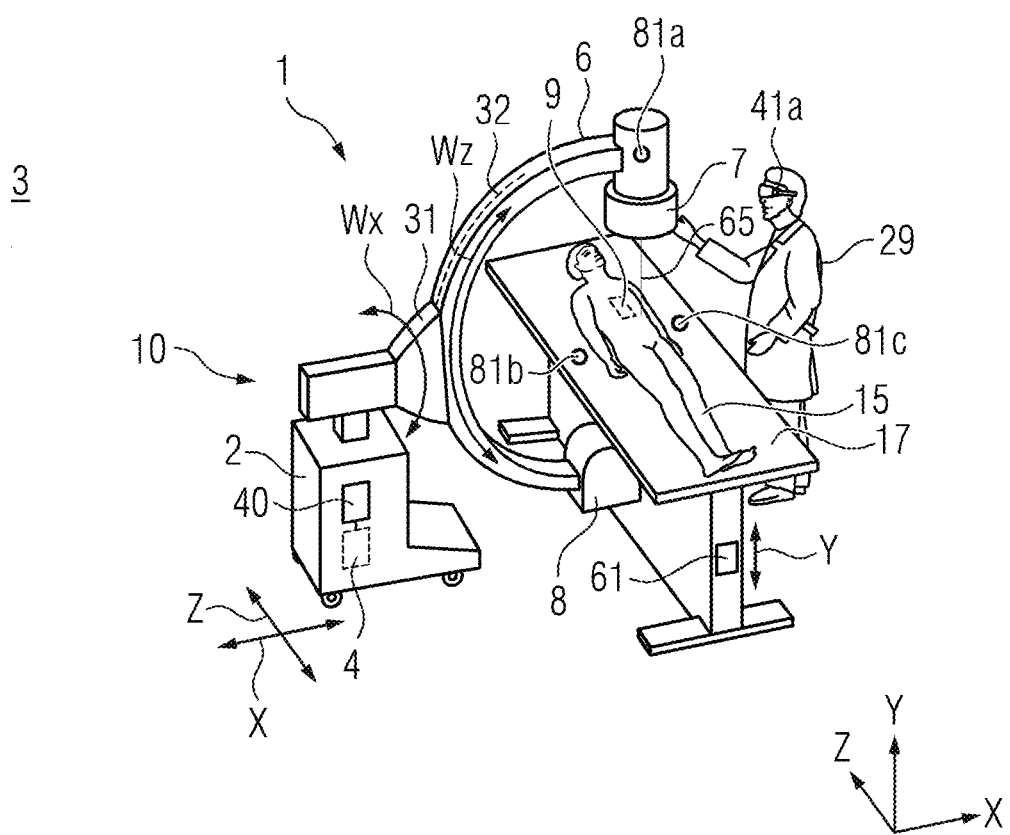
FIG. 3 shows a schematic representation of a system according to an exemplary embodiment of the disclosure.

FIG. 3 shows an embodiment variant in which the imaging apparatus 10 of the inventive system 1 is embodied as an x-ray device 10 with a C-arm 6. An x-ray source 7 and an x-ray detector 8 are arranged opposite each other on the C-arm. The x-ray source 7 and the x-ray detector 8 together form an emitter/detector arrangement of the x-ray device 10. The C-arm 6 of the x-ray device 10 is aligned such that a target region 9 of a patient 15 who is positioned on a patient table 17 can be recorded. By means of the C-arm 6, the x-ray source 7 and the x-ray detector 8 can be moved into various recording positions in relation to the patient 15 who is supported on the patient table 17. To this end, the x-ray device 10 can be moved along the spatial directions X and Z by means of a mobile chassis unit 2. The C-arm 6 additionally has a swivel joint 31 which allows rotation of the C-arm 6 in the rotational direction Wx. The C-arm 6 is moreover mounted on the swivel joint 31 by means of a rail system 32 such that the C-arm 6 can be displaced along the rotational direction Wz.

The alignment of the emitter/detector arrangement in relation to the target region 9 of the patient 15 is possible by virtue of the degree of freedom of movement of the C-arm 6 in the directions of rotation Wz and Wx and the degree of freedom of movement of the mobile chassis unit 2 in the spatial directions X and Z. To this end, the user 29 can move the C-arm 6 and the mobile chassis unit 2 manually along the degrees of freedom of movement into the appropriate position. In addition to this, the patient table 17 can also be positioned along the spatial directions X and Z and at a height Y. In the embodiment variant shown in FIG. 1, the patient table 17 has an operating element 61. The operating element 61 is configured to output a control signal as a function of an input from the user 29, in order to move the patient table 17 along the spatial direction Y by a predetermined distance. It is thereby possible to position the target region 9 of the patient 15 in the appropriate position between the x-ray source 7 and the x-ray detector 8. The operating element 61 can of course be located at any position on the patient table 17.

In the embodiment variant shown, the emitter/detector arrangement, the patient 15, the C-arm 6, the mobile chassis unit 2 and the patient table 17 are imaging-relevant components which must be positioned and/or oriented in an appropriate position in order to perform an imaging examination of the target region 9 of the patient 15. In particular, the imaging-relevant components must be positioned in a pre-determined position relative to each other in this case.

For the purpose of identifying the current positions of the imaging-relevant components, use is preferably made of one or more cameras of the data glasses 41a. The camera or cameras can be configured in particular to capture a three-dimensional mapping of the examination space 3 including the x-ray device 10, the patient 15 and the patient table 17. The three-dimensional mapping of the examination space 3 can be transferred to the computing unit 40 and/or the controller 4 by means of a wireless signal connection. It is however equally conceivable for the data glasses 41a to have a computing unit which is configured to process the three-dimensional mapping of the examination space 3. The processing of the three-dimensional mapping of the examination space 3 can include for example recognizing reference points and/or optical markers 81a, 81b and 81c (81a-c) on the emitter/detector arrangement, the patient table 17 and/or the patient 15, said markers allowing a relative position and/or alignment of the imaging-relevant components to be identified. The data glasses 41a can be configured, for example, to determine a distance 65 between the x-ray source 7 and the target region 9 of the patient 15 on the basis of the three-dimensional mapping of the examination space 3. The distance 65 can be predefined as a function of an imaging examination that is to be performed, and can be used as a reference value for identifying a variance between a current position and/or alignment and an appropriate position and/or alignment of the patient table 17 relative to the x-ray source 7.

The computing unit 40 of the x-ray device 10 and/or the computing unit of the data glasses 41a can also be configured to determine a positioning instruction for an imaging-relevant component on the basis of the captured (image) data of the data glasses 41a. The positioning instruction can be output to the user 29 by means of a projector of the data glasses 41a. However, the extended-reality device 41 can equally be embodied as a virtual-reality headset which is positioned on the head of the user 29 and outputs the positioning instruction to the user 29 by means of an integrated visual display.

The user 29 in the present example is a medical professional, in particular a surgeon or a radiologist. In addition to providing a positioning instruction, the extended-reality device 41 can be configured to provide further information concerning the procedure of the imaging examination. In particular, the extended-reality device 41 can have a user interface 44 which is configured inter alia to provide the user 29 with information concerning an imaging parameter, an imaging sequence, a procedure of the imaging examination, a status and/or progress of an imaging sequence and/or of a procedure of the imaging examination. The extended-reality device 41 preferably comprises an input interface which is configured to capture an input from the user 29. An input from the user can relate to an adaptation of an imaging parameter, an imaging sequence or a procedure of the imaging examination. The input from the user 29 can be transferred to the computing unit 40 and/or the controller 4 of the imaging apparatus 10 by means of a wireless signal connection in particular.

The controller 4 is configured to control the x-ray device 10. In particular, the controller 4 can control or coordinate the setting of imaging parameters, agreement of various steps in an image recording and/or image preparation, transfer of data from the camera of the data glasses 41a to the computing unit 40, and transmission of the positioning instruction to the data glasses 41a. In the present embodiment, the computing unit 40 is integrated into the x-ray device 10 and connected to the controller 4. The controller 4 can of course also be embodied as a separate component or mechanically connected to the extended-reality device 41.

The signal connection between the data glasses 41*a* and the computing unit 40 or the controller 4 is preferably embodied in a wireless manner in order to avoid any restriction of a radius of action and/or freedom of movement of the user 29 due to a cable. To this end, the controller 4 and/or the computing unit 40 can have an output interface (not shown) such as for example a WLAN interface, a Bluetooth interface, an infrared interface or similar. The output interface can be configured in particular to wirelessly transfer the positioning instruction for the imaging-relevant component to a corresponding interface of the extended-reality device 41.

FIG. 4 shows a schematic representation of a user interface 44 of the extended-reality device 41, this being embodied as data glasses 41*a*. The user interface 44 includes a projection of information concerning the procedure of the imaging examination onto a viewing pane of the data glasses 41*a*.

In the example shown, the information concerning the procedure of the imaging examination comprises a positioning instruction for the local coil 26 and the patient table 17. The positioning instructions here comprise schematic diagrams or representations of the patient table 17 and the local coil 26 in the appropriate positions (broken lines). The positioning instructions can further comprise directional instructions (for example arrows) or markings (for example color highlighting of the imaging-relevant components to be positioned). The positioning instructions allow the user 29 to move the imaging-relevant components into the appropriate positions and/or alignments. In this case, the positioning instructions for the imaging-relevant components are preferably projected onto the viewing pane of the data glasses 41*a* in such a way that the schematic diagrams, directional instructions and/or color highlighting are positioned in a correct spatial arrangement relative to that section of the examination space 3 which the user 29 sees through the viewing pane of the data glasses 41*a*. The extended-reality device 41 can equally be embodied as a virtual-reality headset which provides the user 29 with a digital mapping of a section of the examination space 3, this being captured by a camera, together with the positioning instructions.

The information concerning the procedure of the imaging examination can also comprise information concerning a status and/or progress of the imaging examination and/or a procedure of the imaging examination. Various information concerning the procedure of the imaging examination can be provided to the user 29 by means of a graphical operating interface, in particular a menu M, for the purpose of selection. For example, a menu M.2 is active in the embodiment variant shown, providing information concerning an appropriate positioning and/or alignment of imaging-relevant components. A progress bar 45 can also be shown, indicating or quantifying a status of the procedure of the positioning of the imaging-relevant components. In comparison, the menu M.1 can provide a graphical operating interface for adapting a parameter or an imaging sequence of the imaging examination, while the menu M.3 comprises an overview of outstanding and/or completed procedures of the imaging examination. Navigation of the user 29 in the menu M can be affected by means of for example a voice control and/or gesture control. For example, the user 29 can select a menu M by moving their hand in the direction of a symbol for the menu M, while following their hand movement through the viewing pane (or real-time image data from a camera in the case of a virtual-reality headset).

FIG. 5 shows a possible flow diagram of an inventive method for providing information concerning a procedure of an imaging examination using an imaging apparatus 10 and an extended-reality device 41.

In an optional step S1, the extended-reality device 41 is registered with the procedure of the imaging examination, said registration comprising the capture S1.1 of registration information by means of a sensor of the extended-reality device 41 and the synchronization S1.2 of the extended-reality device 41 with the imaging apparatus 10 and/or with an imaging-relevant component as a function of the registration information.

For example, during the capture of the registration information, an optical marker 81 of the imaging apparatus 10 and/or of an imaging-relevant component is captured by means of a sensor of the extended-reality device 41. In this case, the registration information can include information which identifies an imaging-relevant component. It is further conceivable for the computing unit 40 of the imaging apparatus 10 and/or of the extended-reality device 41 to be configured to determine a current spatial arrangement of an imaging-relevant component relative to other imaging-relevant components and/or relative to the imaging apparatus 10. The registration information is preferably synchronized with the spatial arrangement of the imaging-relevant component and/or imaging apparatus 10. In this way, a coordinate system which provides a basis for the spatial computing of the extended-reality device 41 can be adjusted to a coordinate system of the examination space 3. This means that positioning instructions and/or schematic diagrams of imaging-relevant components, as illustrated in FIG. 4, can still correctly assign the imaging-relevant components if the user 29 moves in the examination space 3 and/or if the alignment of the extended-reality device 41 changes due to for example turning of the head.

In a step S2, the procedure of the imaging examination is captured by means of the extended-reality device 41.

During the capture of the procedure of the imaging examination, information concerning an imaging examination that is to be performed is preferably transmitted from the imaging apparatus 10 to the extended-reality device 41 by means of a signal connection. The information concerning the imaging examination that is to be performed can include, for example, information concerning a type and/or model of the imaging apparatus 10. It is equally conceivable for the information concerning the imaging examination that is to be performed to include information concerning an imaging sequence that is to be performed, an imaging parameter that is used, a target region 9 of the patient 15 and/or an imaging-relevant component that is employed. In an exemplary embodiment variant, the content of information concerning the procedure of the imaging examination, said information being provided by means of the user interface 44, is specified as a function of the captured procedure of the imaging examination. During preparation of the imaging examination, for example, a menu M.2 (see FIG. 4) can be automatically provided which assists the user 29 in the context of positioning and/or alignment of imaging-relevant components. In a further example, as a function of the procedure of the imaging examination, a menu M.3 can be provided during an imaging sequence and give an overview of a series of outstanding and/or completed imaging sequences. In particular, the capture of the procedure of the imaging examination can take place automatically. To this end, the extended-reality device 41 can be configured to capture an action of the user 29 and/or a status of a procedure of the imaging examination by means of the sensor, and adapt the information concerning the procedure of the imaging examination accordingly.

In an optional step S3, a current position and/or orientation of the imaging-relevant component is captured by means of a sensor of the extended-reality device 41.

The capture of the current position and/or orientation of an imaging-relevant component can be affected, as shown in FIGS. 1 to 3, in particular by means of a camera or a plurality of cameras of the extended-reality device 41 and/or imaging apparatus 10. In particular, it is conceivable for the capture of the current position and/or orientation of the imaging-relevant component to be affected as a function of one or more optical markers 81 which are positioned on the imaging-relevant components.

In a step S4, information concerning an interaction of a user 29 with an imaging-relevant component is determined as a function of the procedure of the imaging examination.

The determination of the information concerning the interaction of the user 29 with the imaging-relevant component can comprise in particular specifying a positioning instruction or a directional instruction, but also coordinating an output of the extended-reality device 41 with a movement of the user 29.

In a further embodiment variant, the determination of the information concerning the interaction of the user 29 with the imaging-relevant component comprises identifying a variance between the current position and/or orientation of the imaging-relevant component and an appropriate position and/or orientation of the imaging-relevant component. Said variance can be provided to the user 29 as shown in FIG. 4, in particular by means of a schematic diagram of the imaging-relevant component in the appropriate position and/or a directional instruction 90 for positioning and/or aligning the imaging-relevant component.

In a further embodiment variant, the determination of the information concerning the interaction of the user 29 with the imaging-relevant component comprises determining an instruction to the patient 15 as a function of the procedure of the imaging examination, said instruction to the patient 15 comprising at least a respiration instruction and/or guidance for positioning at least a body region of the patient 15. In the case of an imaging examination of a lung and/or tissue in the vicinity of a lung, it is conceivable that the patient 15 is required to pause or suspend respiration during a predetermined phase of an imaging sequence, in order to avoid movement artifacts when recording image data. The respiration of the patient 15 must be precisely coordinated with the predetermined phase of the imaging sequence in this case. The extended-reality device 41 is preferably synchronized with the imaging apparatus 10 by means of a wireless signal connection, such that the instruction to the patient 15 to pause the respiration corresponds at least partially to the predetermined phase of the imaging sequence. The patient 15 can be prepared for the respiratory pause in this case, in particular by means of a countdown, a timer and/or a visual representation of an exemplary respiratory phase. In the case of a plurality of consecutive imaging examinations of different body regions, it is further conceivable for the patient 15 to be guided, by means of the information concerning the interaction of the user 29 with the imaging-relevant component, to adapt a position and/or orientation of a body region. In an embodiment variant, provision of the information concerning the procedure of the imaging examination can include in particular an output of the instruction to the patient 15.

According to a further embodiment variant, the determination of the information concerning the interaction of the user 29 with the imaging-relevant component is affected as a function of the current position and/or orientation of the imaging-relevant component. In this case, the imaging-relevant component can comprise for example a body region of the patient 15, a component of the imaging apparatus and/or a device that is relevant for the imaging examination. A device that is relevant for the imaging examination can be in particular a diagnostically or therapeutically relevant device, but also a device for monitoring the patient 15. The device that is relevant for the imaging examination can also be a medical instrument which is suitable for an invasive or minimally-invasive intervention. Examples of such devices include a wire or sensor of an ECG device, a catheter, a needle, a respiratory belt, a sound generator or other device which is required in order to perform the imaging examination and/or supplements the imaging examination for a further diagnostic purpose.

In step S5 of the inventive method, the information concerning the procedure of the imaging examination is provided by means of a user interface 44 of the extended-reality device 41 as a function of the information that has been determined concerning the interaction of the user 29 with the imaging-relevant component. The information provided to the user 26 concerning the procedure of the imaging examination is preferably updated as a function of the data that is captured by means of the sensor of the extended-reality device 41, either continuously or at discrete time intervals. An interaction of the user 29 with the imaging-relevant component, for example positioning a local coil 26 or respiration of the patient 15, is taken into consideration in this case. It is thus conceivable for even short-term changes in the procedure of the imaging examination to be provided to the user 29.

In an embodiment variant, the variance between the current position and/or orientation of the imaging-relevant component and the appropriate position and/or orientation of the imaging-relevant component is output to the user 29 in the provision of information concerning the procedure of the imaging examination. The variance in this case can be provided as a difference between a position of a virtual schematic diagram of the imaging-relevant component and an imaging-relevant component which is discerned through the viewing pane of the data glasses 41. It is however equally conceivable for the variance to be provided as a difference between a position of a virtual schematic diagram of the imaging-relevant component and a position of the imaging-relevant components as captured by means of a camera in a mapping of the examination space 3. Furthermore, the variance can also be represented as described above by means of a positioning instruction and/or a directional instruction.

In an optional step S6 of the inventive method, an instruction concerning an adaptation of the procedure of the imaging examination is received by means of an input interface of the extended-reality device 41, said adaptation of the procedure of the imaging examination comprising at least an adaptation of a parameter of the imaging examination, an imaging sequence and/or a parameter of an imaging sequence. The adaptation of the procedure of the imaging examination can be affected by the user 29 as described with reference to FIG. 4.

The embodiment variants of the inventive method and the imaging apparatus described herein are naturally understood to be exemplary. Individual embodiment variants can therefore be supplemented by features of other embodiment variants. In particular, the sequence of the method steps of the inventive method is understood to be exemplary. The individual steps can also be performed in a different sequence or overlap each other temporally in part or completely.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. An extended-reality device comprising:
an interface configured to capture a procedure of an imaging examination using an imaging apparatus;
a sensor configured to capture a current position and/or orientation of an imaging-relevant component;
a user interface configured to be: shaped according to a body region of a user and/or mechanically fastened to the body region of the user; and
a computing unit configured to:
determine information concerning the procedure of the imaging examination, the information concerning the procedure including an appropriate position and/or orientation of the imaging-relevant component;
determine information concerning an interaction of the user with the imaging-relevant component based on the information concerning the procedure and the current position and/or orientation of the imaging-relevant component, wherein the information concerning the interaction of the user with the imaging-relevant component includes a variance between the current position and/or orientation of the imaging-relevant component and the appropriate position and/or orientation of the imaging-relevant component; and
provide, using the user interface and based on the information concerning the interaction, the information concerning the procedure to the user of the extended-reality device.

2. The extended-reality device as claimed in claim 1, wherein the sensor is an optical sensor configured to capture the position and/or orientation of the imaging-relevant component as a function of at least one optical marker positioned on the imaging-relevant component and/or the extended-reality device.

3. The extended-reality device as claimed in claim 1, further comprising an input interface configured to capture an instruction from the user concerning an adaptation of the imaging examination, wherein the extended-reality device is configured to transfer the instruction from the user concerning the adaptation of the imaging examination to the imaging apparatus.

4. The extended-reality device as claimed in claim 1, wherein:
the user interface is further configured to provide the user with information concerning an execution and/or current status of the procedure of the imaging examination, and
the extended-reality device further comprises an input interface configured to receive an input from the user concerning the procedure of the imaging examination.

5. The extended-reality device as claimed in claim 1, wherein the extended-reality device is a virtual-reality headset configured to provide the user with a virtual environment using the user interface.

6. A system comprising:
an imaging apparatus; and
an extended-reality device including:
a sensor configured to capture a current position and/or orientation of an imaging-relevant component;
an input interface configured to receive, from a user, from the user an input concerning the procedure of the imaging examination; and
a computing device configured to:
determine the information concerning a procedure of an imaging examination using the imaging apparatus, the information concerning the procedure including an appropriate position and/or orientation of the imaging-relevant component; and
determine information concerning an interaction of the user with the imaging-relevant component based on the information concerning the procedure and the current position and/or orientation of the imaging-relevant component, wherein the information concerning the interaction of the user with the imaging-relevant component includes a variance between the current position and/or orientation of the imaging-relevant component and the appropriate position and/or orientation of the imaging-relevant component; and
a user interface configured to provide, based on the information concerning the interaction, the user with the information concerning the procedure.

7. The system as claimed in claim 6, further comprising another extended-reality device, wherein the computing unit is configured to determine information concerning a task of a first user and to provide the information to a second user using the other extended-reality device, wherein the information which is provided to the second user and concerns the task of the first user differs from information which concerns the procedure of the imaging examination and is provided to the first user using the user interface of the extended-reality device.

8. A method for providing information concerning a procedure of an imaging examination using a system that includes an imaging apparatus with an extended-reality device, the method comprising:
capturing the procedure of the imaging examination using an interface of the extended-reality device;
capturing a current position and/or orientation of an imaging-relevant component by a sensor of the extended-reality device;
determining, using a computing unit of the extended-reality device, information concerning an interaction of a user with the imaging-relevant component based on the procedure of the imaging examination and the current position and/or orientation of the imaging-relevant component, wherein determining the information concerning the interaction of the user with the imaging-relevant component includes identifying a variance between the current position and/or orientation of the imaging-relevant component and an appropriate position and/or orientation of the imaging-relevant component; and
providing, based on the determined information concerning the interaction of the user with the imaging-relevant component, the information concerning the procedure of the imaging examination to the user using a user interface of the extended-reality device, wherein providing the information concerning the procedure of the imaging examination includes outputting the variance between the current position and/or orientation of the imaging-relevant component and the appropriate position and/or orientation of the imaging-relevant component.

9. The method as claimed in claim 8, further comprising:
registering the extended-reality device with the procedure of the imaging examination, wherein the registering comprises:
capturing registration information by the sensor of the extended-reality device, and
synchronizing the extended-reality device with the imaging apparatus and/or an imaging-relevant component as a function of the registration information.

10. The method as claimed in claim 8, wherein:
the user is a patient, the determination of the information concerning the interaction of the user with the imaging-relevant component includes determining an instruction to the patient as a function of the procedure of the imaging examination,
the instruction to the patient comprises at least a respiration instruction and/or guidance for positioning at least a body region of the patient,
the provision of the information concerning the procedure of the imaging examination comprises an output of the instruction to the patient.

11. The method as claimed in claim 8, wherein providing the information concerning the procedure of the imaging examination includes providing information concerning progress and/or a current status of the procedure of the imaging examination.

12. The method as claimed in claim 8, further comprising:
receiving an instruction concerning an adaptation of the procedure of the imaging examination by an input interface of the extended-reality device, the adaptation of the procedure of the imaging examination including at least an adaptation of a parameter of the imaging examination, an imaging sequence and/or a parameter of an imaging sequence.

13. A non-transitory computer program product which is directly loadable into a memory of a controller of the imaging apparatus, when executed by the controller, causes the imaging apparatus to perform the method as claimed in claim 8.

14. A non-transitory computer-readable storage medium with an executable program stored thereon, that when executed, instructs a processor to perform the method of claim 8.

15. The method as claimed in claim 8, wherein the imaging-relevant component comprises: a body region of a patient, a component of the imaging apparatus, and/or a device that is diagnostically relevant for the imaging examination.

\* \* \* \* \*